US009498140B2

(12) United States Patent
Magrath et al.

(10) Patent No.: US 9,498,140 B2
(45) Date of Patent: Nov. 22, 2016

(54) IMAGE-BASED WAVEFORM PARAMETER ESTIMATION

(71) Applicants: Siemens Medical Solutions USA, Inc., Malvern, PA (US); Northwestern University, Evanston, IL (US)

(72) Inventors: Patrick Magrath, Chicago, IL (US); Bruce S. Spottiswoode, Chicago, IL (US); Aurélien Stalder, Erlangen (DE); Mehmet Akif Gulsun, Princeton, NJ (US); Michael Markl, Chicago, IL (US)

(*) Notice: Subject to any disclaimer, the term of this patent is extended or adjusted under 35 U.S.C. 154(b) by 0 days.

(21) Appl. No.: 14/704,126

(22) Filed: May 5, 2015

(65) Prior Publication Data

US 2015/0324977 A1    Nov. 12, 2015

Related U.S. Application Data

(60) Provisional application No. 61/991,071, filed on May 9, 2014.

(51) Int. Cl.
*A61B 5/00* (2006.01)
*A61B 5/0285* (2006.01)
*G06T 7/00* (2006.01)
*A61B 5/026* (2006.01)

(52) U.S. Cl.
CPC .......... *A61B 5/0285* (2013.01); *A61B 5/0263* (2013.01); *G06T 7/0012* (2013.01); *G06T 7/0016* (2013.01); *G06T 7/0083* (2013.01); *G06T 2207/10088* (2013.01); *G06T 2207/20101* (2013.01); *G06T 2207/30104* (2013.01); *G06T 2207/30172* (2013.01)

(58) Field of Classification Search
CPC ...... A61B 8/06; A61B 8/13; A61B 5/02007; A61B 8/483; A61B 5/0285; A61B 5/02125; A61B 8/0891; A61B 5/0261; A61B 5/055; A61B 8/04; A61B 8/5223; A61B 5/489; A61B 8/085; A61B 5/0066; A61B 5/0263; A61B 5/0295; A61B 8/463; A61B 5/022; A61B 3/1233; A61B 5/021; A61B 5/026; A61B 5/107; A61B 5/7278; A61B 5/7285; A61B 8/5207; A61B 1/3137; A61B 2017/00778; A61B 5/02405; G01S 15/8993; G01S 15/8984; G01S 15/8988; G01S 7/52066; G01S 15/8963; G06T 2207/30104; G06T 7/0012; G06T 2207/10096; G06T 7/204; G06T 7/2046; G01N 15/05
See application file for complete search history.

(56) References Cited

U.S. PATENT DOCUMENTS

| 4,476,874 A * | 10/1984 | Taenzer | A61B 8/06 600/441 |
|---|---|---|---|
| 4,602,641 A * | 7/1986 | Feinberg | A61B 5/0263 324/306 |
| 6,176,832 B1 * | 1/2001 | Habu | A61B 5/0285 600/485 |

(Continued)

*Primary Examiner* — Manav Seth

(57) ABSTRACT

Disclosed herein is a framework for facilitating waveform parameter estimation. In accordance with one aspect, time-based waveforms are generated based on analysis planes positioned along a centerline of the vessel. A surface may be fitted to upslope regions of the waveforms to determine one or more waveform parameters based on intersection of the surface with the upslope regions.

20 Claims, 4 Drawing Sheets

(56) References Cited

U.S. PATENT DOCUMENTS

| | | | | |
|---|---|---|---|---|
| 6,647,135 B2* | 11/2003 | Bonnefous | A61B 8/06 | 128/916 |
| 6,682,483 B1* | 1/2004 | Abend | G01S 7/52026 | 128/916 |
| 7,044,913 B2* | 5/2006 | Shiki | A61B 8/06 | 600/437 |
| 7,238,158 B2* | 7/2007 | Abend | G01S 7/52026 | 600/454 |
| 7,534,209 B2* | 5/2009 | Abend | G01S 7/52026 | 600/454 |
| 8,282,559 B2* | 10/2012 | Njemanze | A61B 8/06 | 600/453 |
| 8,675,940 B2* | 3/2014 | Gulsun | G06T 7/2046 | 382/131 |
| 2006/0009710 A1* | 1/2006 | Bernstein | A61B 5/02028 | 600/547 |
| 2007/0248250 A1* | 10/2007 | Gulsun | G06K 9/342 | 382/128 |
| 2008/0249755 A1* | 10/2008 | Tek | A61B 5/02014 | 703/11 |
| 2008/0275351 A1* | 11/2008 | Kirchberg | A61B 5/0285 | 600/500 |
| 2009/0278846 A1* | 11/2009 | Gulsun | G06T 7/0085 | 345/423 |
| 2011/0103665 A1* | 5/2011 | Gulsun | G06T 7/2046 | 382/131 |

* cited by examiner

IMAGE-BASED WAVEFORM PARAMETER ESTIMATION

CROSS-REFERENCE TO RELATED APPLICATION

This application claims the benefit of U.S. provisional application No. 61/991,071 filed on May 9, 2014, the entire contents of which are incorporated herein by reference.

TECHNICAL FIELD

The present disclosure generally relates to diagnostic imaging and, more specifically, to automated or semi-automated systems and methods for facilitating estimation of waveform parameters based on diagnostic images.

BACKGROUND

Pulse wave velocity (PWV) is a measure of arterial stiffness or vessel compliance. PWV is a strong indicator of atherosclerosis and vessel stiffness, as well as cardiovascular events and all-cause mortality. PWV estimation may involve measuring the arrival of blood at several points along a vessel, and calculating velocity using these time points and length of the vessel. Traditionally, pulse wave velocity is measured using ultrasound or catheterization to determine pulse pressure. Both of these methods have significant drawbacks. For example, catheterization is highly invasive, while ultrasound distance measurements can be highly inaccurate, resulting in error of as much as 30%.

More recently, phase contrast magnetic resonance imaging (MRI) with multiple acquisition planes has been used to non-invasively measure PWV. A variety of two-dimensional (2D) phase contrast MRI techniques for PWV extraction have been established. While these methods have shown reasonable agreement with literature values, they do have pronounced limitations. For example, existing models for calculation of PWV, such as time-to-foot (TTF) analysis and cross correlation of the flow waveforms, suffer from high variability. Some studies have explored a more comprehensive approach to PWV analysis: plane fitting of flow waveform upslope regions. However, such plane fitting may systematically underestimate PWV, because the gradient of the blood velocity/flow upslope varies along the vessel. Therefore, analysis of this data and reliable calculation of PWV has previously remained challenging.

SUMMARY

The present disclosure relates to a framework for facilitating waveform parameter estimation. In accordance with one aspect, time-based waveforms are generated based on analysis planes positioned along a centerline of the vessel. A surface may be fitted to upslope regions of the waveforms to determine one or more waveform parameters based on intersection of the surface with the upslope regions.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
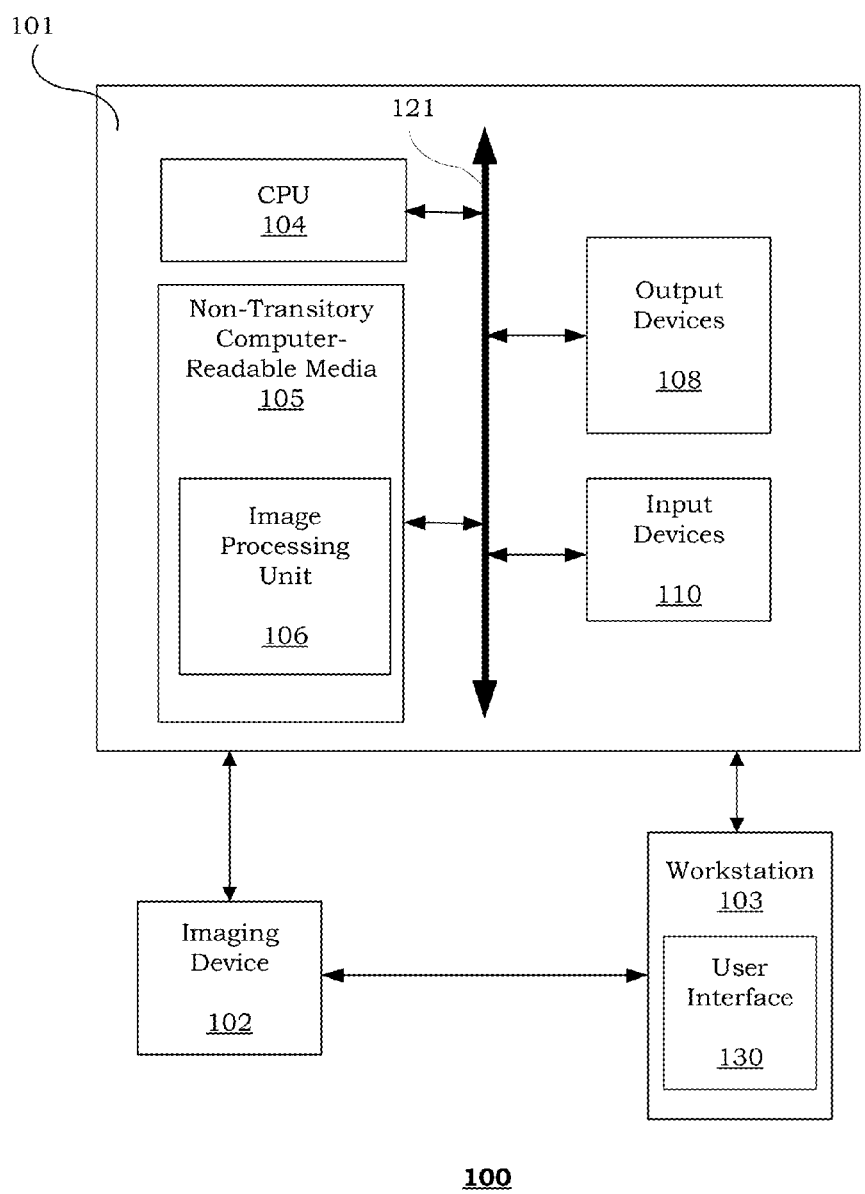
FIG. 1 is a block diagram illustrating an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, MRI imaging data may be used herein as an exemplary imaging modality. It will be appreciated, however, that data from any type of imaging modality including, but not limited to, X-Ray radiographs, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system's memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2D images, voxels for 3D images, doxels for 4D images, etc.). The image may be, for example, a medical image of a subject collected by computed tomography, magnetic resonance imaging, ultrasound, or any other medical imaging system known to one of skill in the art. The image may also be provided from non-medical contexts, such as remote sensing systems, electron microscopy, etc. The methods of the inventions can be applied to images of any dimension, e.g., a 2D picture, 3D or 4D volume. For a 2- or 3-dimensional image, the domain of the image is typically a 2- or 3-dimensional rectangular array, wherein each pixel or voxel can be addressed with reference to a set of two or three mutually orthogonal axes. The terms "digital" and "digitized" as used herein will refer to images or volumes, as appropriate, in a digital or digitized format acquired via a digital acquisition system or via conversion from an analog image.

A framework for waveform parameter estimation is described herein. In accordance with one aspect, the framework non-invasively extracts waveform parameters (e.g., pulse wave velocity or PWV) by fitting a complex surface to the upslope region of the flow waveform through each flow analysis (or evaluation) plane. In previous work, many analysis planes are acquired in a single vessel and the time required to segment the lumen and calculate centerlines is prohibitive. The present framework advantageously uses semi-automated centerline extraction and vessel segmentation to place a large number of flow analysis planes along the vessel with minimal user interaction. In addition, by employing more complex and robust fitting strategies of the waveform upslope, the present framework advantageously improves both accuracy and reproducibility when deriving flow waveform parameters from, for example, 4D-flow MRI data, using multiple analysis planes. The non-linearity of the blood arrival time and the waveform upslope along a vessel is more accurately captured, particularly in cases with pathology. These exemplary advantages and features will be described in further details in the following description.

For purposes of illustration, the present framework may be described in the context of determining pulse wave velocity. It should be appreciated, however, the present framework may also be used to determine other waveform parameters, such as flow per cardiac cycle, regurgitant flow ratio, resistance index, pulsatility index, pressure, and so forth. The framework is applicable to any vessel containing flowing material, including but not limited to ex vivo and non-MRI flow, velocity, pressure measurements, etc.

FIG. 1 is a block diagram illustrating an exemplary system 100. The system 100 includes a computer system 101 for implementing the framework as described herein. The computer system 101 may further be connected to an imaging device 102 and a workstation 103, over a wired or wireless network. The imaging device 102 may be a radiology scanner such as a magnetic resonance (MR) scanner, PET/MR, X-ray or a CT scanner.

Computer system 101 may be a desktop personal computer, a portable laptop computer, another portable device, a mini-computer, a mainframe computer, a server, a storage system, a dedicated digital appliance, or another device having a storage sub-system configured to store a collection of digital data items. In some implementations, computer system 101 comprises a processor or central processing unit (CPU) 104 coupled to one or more non-transitory computer-readable media 105 (e.g., computer storage or memory), output devices 108 (e.g., monitor, display, printer, etc.) and various input devices 110 (e.g., mouse, keyboard, touch pad, voice recognition module, etc.) via an input-output interface 121. Computer system 101 may further include support circuits such as a cache, a power supply, clock circuits and a communications bus. Furthermore, computer system 101 may be provided with a graphics controller chip, such as a graphics processing unit (GPU) that supports high performance graphics functions.

It is to be understood that the present technology may be implemented in various forms of hardware, software, firmware, special purpose processors, or a combination thereof. In one implementation, the techniques described herein are implemented by image processing unit 106. Image processing unit 106 may include computer-readable program code tangibly embodied in non-transitory computer-readable media 105. Non-transitory computer-readable media 105 may include random access memory (RAM), read only memory (ROM), magnetic floppy disk, flash memory, and other types of memories, or a combination thereof. The computer-readable program code is executed by CPU 104 to control and/or process image data from imaging device 102.

As such, the computer system 101 is a general-purpose computer system that becomes a specific-purpose computer system when executing the computer readable program code. The computer-readable program code is not intended to be limited to any particular programming language and implementation thereof. It will be appreciated that a variety of programming languages and coding thereof may be used to implement the teachings of the disclosure contained herein. Computer system 101 may also include an operating system and microinstruction code. The various techniques described herein may be implemented either as part of the microinstruction code or as part of an application program or software product, or a combination thereof, which is executed via the operating system. Various other peripheral devices, such as additional data storage devices and printing devices, may be connected to the computer system 101.

The workstation 103 may include a computer and appropriate peripherals, such as a keyboard and display, and can be operated in conjunction with the entire system 100. For example, the workstation 103 may communicate with the imaging device 102 so that the image data acquired by, for instance, imaging device 102 can be rendered at the workstation 103 and viewed on the display. The workstation 103 may include a user interface 130 that allows a radiologist or any other skilled user (e.g., physician, technician, operator, scientist, etc.) to manipulate and view the image data. Further, the workstation 103 may communicate directly with computer system 101 to present acquired, reconstructed and/or processed image data. For example, a radiologist can interactively manipulate the displayed representation of the processed image data and view it from various viewpoints and in various reading modes.

Figure 2:
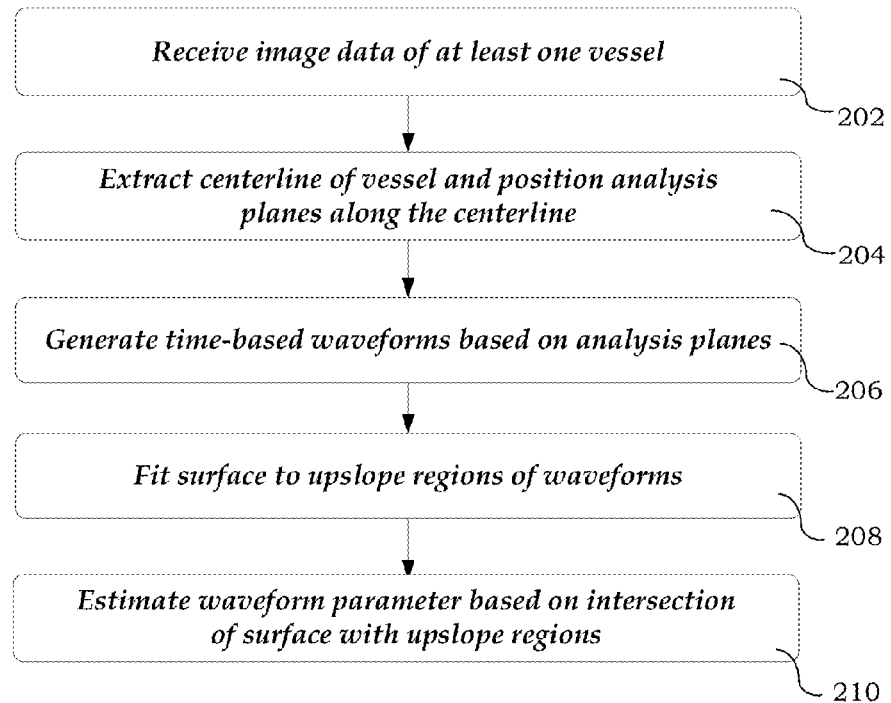
FIG. 2 shows an exemplary method of determining at least one waveform parameter.

FIG. 2 shows an exemplary method 200 of determining at least one waveform parameter. It should be noted that the steps of the method 200 may be performed in the order shown or a different order. Furthermore, different, additional or fewer steps may be implemented. Moreover, the method 200 may be implemented with the system 100 of FIG. 1, a different system, or a combination thereof.

At 202, image processing unit 106 receives image data of at least one vessel from imaging device 102. The image data may be acquired from one subject (e.g., a patient) or multiple subjects. The image data may be acquired based on contrast-enhanced magnetic resonance images and/or non-contrast enhanced angiography (MRA) data of blood vessels (e.g., Time of Flight (TOF) or otherwise labeled flowing spins). The image data may be time-resolved images (e.g., two-dimensional (2D), three-dimensional (3D), or four-dimensional (4D)) captured at different periods of time. For example, four-dimensional (4D) flow MRI data may be acquired to utilize the information provided by the full volumetric coverage of the vessel. Other types of image data are also useful. Exemplary vessels include, but are not limited to, blood vessels (e.g., artery, aortic arch, capillary, etc.), cerebrospinal fluid (CSF) channels, lymphatic vessels, or any other types of vessels containing in vivo or in vitro flowing fluid or material.

At 204, image processing unit 106 extracts the centerline of the vessel in the image data and positions analysis planes along the extracted centerline. In some implementations, the vessel segmentation or centerline extraction is performed semi-automatically (or automatically) so that a large number of analysis (or evaluation) planes may be automatically positioned along the centerline with minimal user interaction. An exemplary segmentation technique is described in U.S. Pat. No. 8,675,940, which is herein incorporated by reference.

Figures 3A, 3B, 3C:
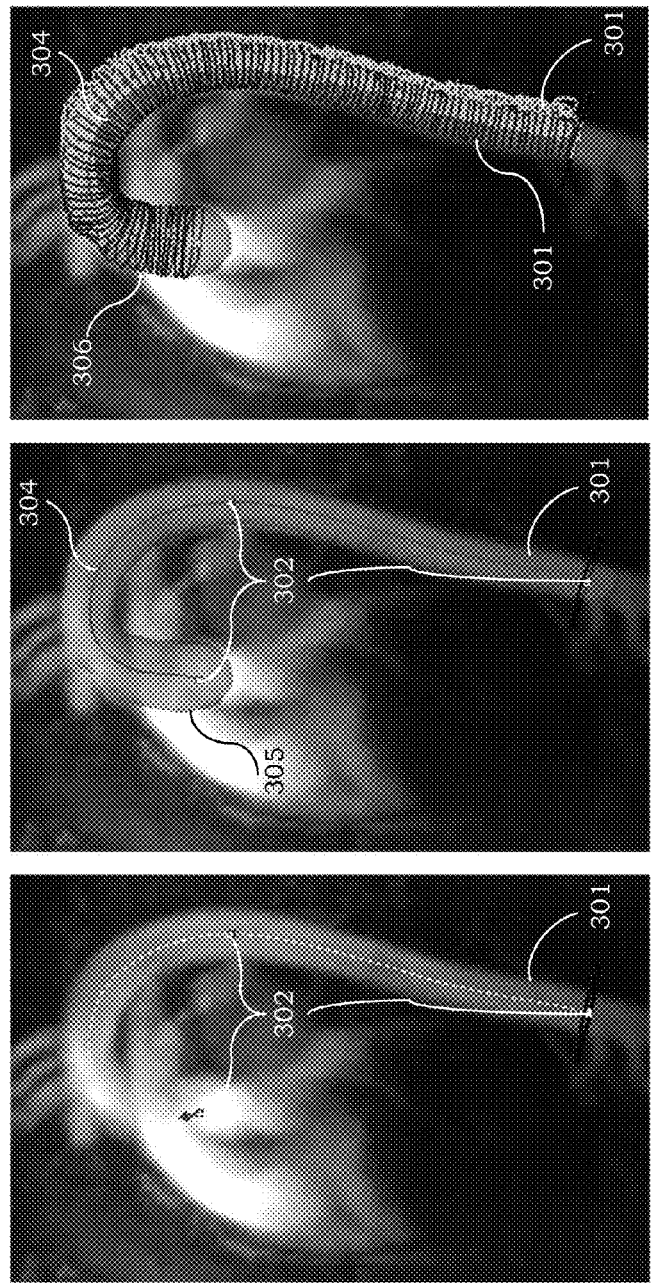
FIGS. 3a-c illustrate an exemplary method of vessel segmentation and analysis plane placement.

FIGS. 3a-c illustrate an exemplary semi-automated method of vessel segmentation and analysis plane placement. It should be appreciated that other methods may also be used. In FIG. 3a, a user initially places seed points 302 on an image of the vessel 301. This may be performed via, for example, user interface 130. In FIG. 3b, the centerline 304 within the lumen of vessel 301 is automatically detected between the user-placed seed points 302. The vessel boundary or contour (e.g., vascular lumen) 305 of the vessel 301 may be automatically extracted using the detected centerline 304. Alternatively, the vessel segmentation may be performed in a completely automatic manner using a classifier trained to identity vessels and vessel centerlines.

In FIG. 3c, multiple analysis (or evaluation) planes are positioned along the centerline 304 for generating anatomy contours 306. Multiple analysis planes separated by a predetermined distance may be derived by automatically sampling points along the centerline of the vessel 301. An analysis plane is a cross-section of the vessel 301 that is perpendicular to the centerline and derived by calculating the tangent of the centerline at that location. For example, two points along a centerline of an image of a vessel can be sampled to create a line segment, and a plane perpendicular to that line segment can be derived. Two different points along the center line can then be sampled to create a new line segment, and a new plane perpendicular to that new line segment can then be derived. The sampling along the center line of the model can be repeated for the entire length of the vessel to generate additional analysis planes as needed.

Returning to FIG. 2, at 206, image processing unit 106 generates time-based waveforms based on the analysis planes. A time-based waveform is a shape of a time-varying signal at a particular sampled point or distance along the vessel. In some implementations, the time-based waveform is a flow waveform that represents the shape of a flow signal that varies with time (e.g., blood flow measured in milliliters per second). Other types of time-varying waveforms, such as a velocity waveform that represents the shape of a velocity signal that varies with time, may also be generated.

Figure 4:
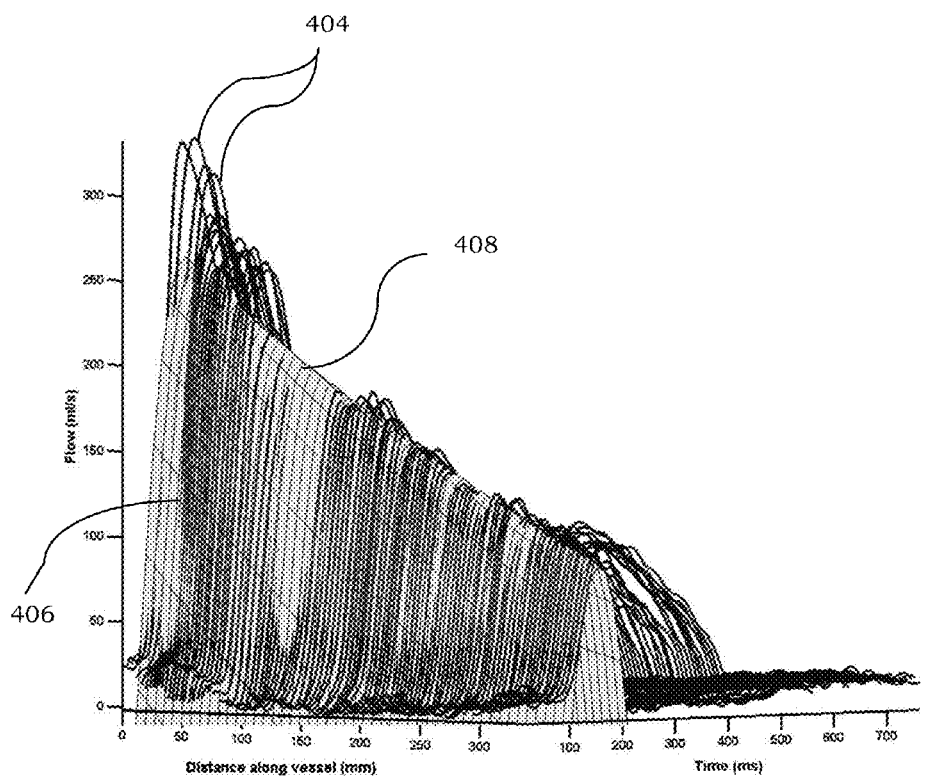
FIG. 4 shows an exemplary graphical plot of multiple flow waveforms.

FIG. 4 shows an exemplary three-dimensional graphical plot of multiple flow waveforms 404. The flow waveforms 404 are sampled at multiple points along the vessel with a predetermined delay time therebetween. The upslope region 406 of each flow waveform represents an increase in flow (or velocity). Arterial distensibility may be estimated based on such upslope events. For example, PWV may be effectively determined by measuring the time that the upslope occurs as a function of distance along the vessel. For a rigid (or non-distensible) vessel wall, the PWV is typically faster than for a distensible wall.

Returning to FIG. 2, at 208, image processing unit 106 fits a surface to the upslope regions of the time-based waveforms. The surface may be a complex surface that advantageously captures the non-linearity of blood arrival time and waveform upslope along a vessel more accurately. The surface may be, for example, a $2^{nd}$ order or a higher order (e.g., $3^{rd}$ order) polynomial surface. A non-polynomial surface, such as a spline surface, composition of basis functions surface, etc., may also be used.

In some implementations, the surface includes a "twisted plane" that models the changing upslopes as a function of distance along the vessel, thereby better approximating PWV than a simple least squares plane. The twisted plane is an extension of the simple least squares plane with an additional degree of freedom, allowing it to deform, for example, in the z direction in addition to the x- and y-directions (i.e., three-dimensional). By analyzing the intersection of this twisted plane with the foot of the upslope region, PWV or other type of waveform parameter can be derived.

In some implementations, a sliding window may be used to derive local waveform parameters along a series of analysis planes along the vessel, thereby more closely conforming to local changes in geometry and vessel compliance that might impact global waveform parameter. In some implementations, multiple least squares planes are used to fit different subsets of the waveforms within the sliding window to generate multiple local waveform parameters, which are then used to derive a global waveform parameter. Other types of surfaces may also be used.

In other implementations, the upslopes of the waveforms are fitted to a second order polynomial surface represented by the following:

$$f(x,t)=A+Bx+Ct+Dx^2+Ext+Ft^2 \quad (1)$$

wherein x denotes the centerline distance, t denotes the time, f(x,t) denotes the flow rate, and A, B, C, D, E and F are parameters extracted from the fitting. This allows some freedom of movement in the X, Y, and Z directions (i.e., three dimensional). Such polynomial fitting scheme could be extended almost indefinitely to higher orders if desired.

FIG. 4 shows an exemplary nonlinear least squares fit plane 408 that intersects with the upslope regions 406 of the flow waveforms 404, allowing for a derivation of mean PWV in the thoracic aorta. The velocities at the intersection of the surface 408 with the foot of the upslope region 406 (calculated, for example, with a linear fit of the flow=0 intersection data) closely resemble the changing flow profile over time and can be used to calculate mean PWV.

Returning to FIG. 2, at 210, image processing unit 106 estimates one or more waveform parameters based on the intersection of the surface with the upslope regions. In some implementations, the one or more waveform parameters are derived using intersection points of the surface with the foot or beginning of the upslope regions. The waveform parameters may include, but are not limited to, pulse wave velocity, flow per cardiac cycle, velocity per cardiac cycle, regurgitant flow ratio, resistance index, pulsatility index, and so forth. The waveform parameters may be a series of local parameter values or a global parameter value (e.g., average or mean) over large segments of the vessel. The estimated waveform parameters may be presented in the form of, for example, a diagnostic report displayed by user interface 130 or output device 108. Other forms of presentation, such as a printed report, are also useful.

The proposed high sampling density of flow profiles advantageously allows for a robust and accurate fit with a detailed resolution of PWVs along the vessel. For global PWV measurements, the proposed fitting can be applied to data from any phase contrast MRI acquisition technique (2D, 3D, or 4D) where blood flow through a vessel is measured as it passes through more than one analysis plane separated by a predetermined distance.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A method for determining a property of a biological vessel based on an improved estimation of a waveform parameter, comprising:
   (i) receiving image data of the biological vessel;
   (ii) determining a centerline of the biological vessel based on the image data and generating a plurality of analysis planes that lie perpendicular to the centerline;
   (iii) generating time-based waveforms based on the analysis planes;
   (v) fitting surfaces to upslope regions of different subsets of the waveforms to derive local waveform parameters based on intersections of the surfaces with the upslope regions; and
   (v) determining a global waveform parameter based on the local waveform parameters;
   wherein the global waveform parameter is associated with the property of the biological vessel.

2. The method of claim 1 wherein fitting the surfaces to the different subsets of the upslope regions comprises fitting least squares planes to the different subsets of the upslope regions.

3. The method of claim 1 wherein determining the global waveform parameter comprises determine an average value of the local waveform parameters.

4. The method of claim 1 wherein the global waveform parameter comprises at least one of a pulse wave velocity, a flow per cardiac cycle, a regurgitant flow ratio, a resistance index, and a pulsatility index.

5. A system for determining a property of a biological vessel based on an improved estimation of a waveform parameter, comprising:
   a non-transitory memory device for storing computer readable program code, and
   a processor in communication with the memory device, the processor being operative with the computer readable program code to perform steps including:
   (i) receiving image data of at least one the biological vessel;
   (ii) determining a centerline of the biological vessel based on the image data and generating a plurality of analysis planes that lie perpendicular to the centerline;
   (iii) generating time-based waveforms based on the analysis planes positioned along a centerline of the vessel;
   (v) fitting surfaces to upslope regions of different subsets of the time-based waveforms to derive local waveform parameters based on intersections of the surfaces with the upslope regions; and
   (v) determining a global waveform parameter based on the local waveform parameters;
   wherein the global waveform parameter is associated with the property of the biological vessel.

6. The system of claim 5 wherein the image data comprises four-dimensional flow magnetic resonance image data.

7. The system of claim 5 wherein the biological vessel comprises a blood vessel.

8. The system of claim 5 wherein the centerline of the vessel is determined by automatically detecting the centerline between user-placed seed points.

9. The system of claim 5 wherein the time-based waveforms comprise time-based flow waveforms.

10. The system of claim 5 wherein the time-based waveforms comprise time-based velocity waveforms.

11. The system of claim 5 wherein the surface comprises a polynomial surface having an order that is greater than or equal to 2.

12. The system of claim 11 wherein the polynomial surface is represented by $$f(x,t)=A+Bx+Ct+Dx^2+Ext+Ft^2,$$

wherein x denotes a distance along the centerline, t denotes time, f(x,t) denotes flow rate, and A, B, C, D, E and F denote parameters extracted from the fitting.

13. The system of claim 5 wherein the surface comprises a twisted plane that represents changes in the upslopes as a function of distance along the centerline.

14. The system of claim 5 wherein the processor is operative with the computer readable program code to fit the surface to the upslope regions by fitting multiple surfaces to different subsets of the upslope regions to derive a plurality of local waveform parameters.

15. The system of claim 14 wherein the global waveform parameter comprises at least one of a pulse wave velocity, a flow per cardiac cycle, a regurgitant flow ratio, a resistance index and a pulsatility index.

16. The system of claim 14 wherein surfaces comprise least square planes.

17. The system of claim 5 wherein the surfaces comprise at least one of spline surfaces and composition of basis functions surfaces.

18. The system of claim 5, further comprising an imaging device configured to provide the image data.

19. The system of claim 17, wherein the imaging device comprises a magnetic resonance imaging arrangement.

20. The system of claim 17, wherein the imaging device comprises at least one of an x-ray arrangement, a CT scanner, and a positron emission tomography scanner.

* * * * *